United States Patent [19]
Aksela et al.

[11] Patent Number: 6,093,849
[45] Date of Patent: Jul. 25, 2000

[54] N-BIS- OR N-TRIS-[(1,2-DICARBOXY-ETHOXY)-ETHYL]-AMINE DERIVATIVES AND PREPARATION AND USE OF THE SAME

[75] Inventors: Reijo Aksela; Ilkka Renvall, both of Espoo; Arto Paren, Valkeakoski, all of Finland

[73] Assignee: Kemira Chemicals Oy, Helsinki, Finland

[21] Appl. No.: 09/194,310

[22] PCT Filed: May 30, 1997

[86] PCT No.: PCT/FI97/00332

§ 371 Date: Nov. 24, 1998

§ 102(e) Date: Nov. 24, 1998

[87] PCT Pub. No.: WO97/45396

PCT Pub. Date: Dec. 4, 1997

[30] Foreign Application Priority Data

May 30, 1996 [FI] Finland ................................ 962261

[51] Int. Cl.⁷ ................................................ C07C 229/22
[52] U.S. Cl. ................................................ 562/568
[58] Field of Search ................................ 562/568

[56] References Cited

U.S. PATENT DOCUMENTS 4,044,034  8/1977  Christiansen ..................... 260/404.5

FOREIGN PATENT DOCUMENTS

| 05320003 | 3/1993 | European Pat. Off. . |
| 6282044 | 7/1994 | Japan . |
| 7120894 | 5/1995 | Japan . |
| 7120899 | 5/1995 | Japan . |
| 7261355 | 10/1995 | Japan . |

OTHER PUBLICATIONS

Finnish Patent Application No. 960755, filed Feb. 19, 1996.
Finnish Patent Application No. 960756, filed Feb. 19, 1996.
Finnish Patent Application No. 960757, filed Feb. 19, 1996.
Finnish Patent Application No. 960758, filed Feb. 19, 1996.

*Chemical Abstracts*, vol. 84, No. 20, May 17, 1976 (May 17, 1976), (Columbus, Ohio, USA), p. 122, The Abstract No. 137608h,, JP, 7602708 A, (Okumura, Osamu et al), Jan. 10, 1976 (Jan. 10, 1976).

*Chemical Abstracts*, vol. 123, No. 16, Oct. 16, 1995 (Oct. 16, 1995), (Columbus, Ohio, USA), p. 1024, The Abstract No. 212991, JP, 71208949 A, (Okada, Hisashi et al) May 12, 1995 (May 12, 1995).

J. van Westrenen et al., The synthesis of polyhydroxycarboxylates, *Recl. Trav. Chem. Pays–Bas*, vol. 109, 1990, p.474–478.

*Primary Examiner*—Johann Richter
*Assistant Examiner*—Brian J. Davis
*Attorney, Agent, or Firm*—Morgan & Finnegan, LLP

[57] ABSTRACT

The invention relates to N-bis- or N-tris-[(1,2-dicarboxy-ethoxy)-ethyl]-amine derivatives having the formula (I)

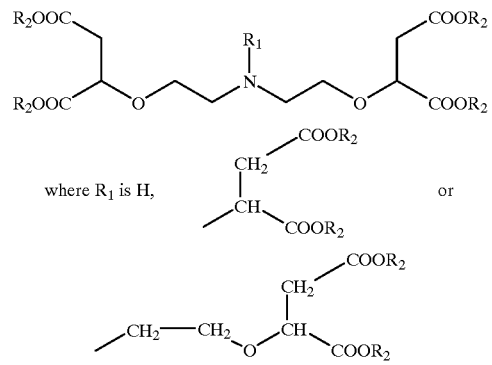

and $R_2$ is hydrogen, an alkali metal or an earth-alkali metal.

The invention also relates to a method for preparing the same and their use as chelating agents.

13 Claims, No Drawings

N-BIS- OR N-TRIS-[(1,2-DICARBOXY-ETHOXY)-ETHYL]-AMINE DERIVATIVES AND PREPARATION AND USE OF THE SAME

This application is a 371 of PCT/FI97/00332 filed May 30, 1997.

The invention relates to novel N-bis- or N-tris-[(1,2-dicarboxy-ethoxy-(ethyl]-amine derivatives and to the preparation and use of the same.

The formula of the novel compounds according to the invention is

Formula I

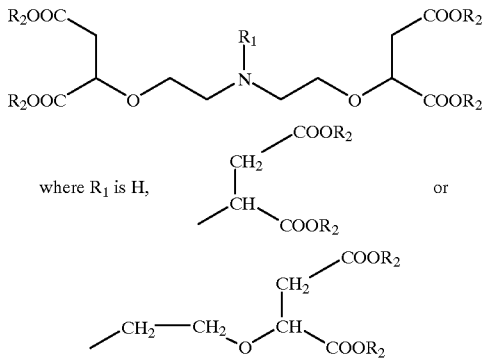

and $R_2$ is hydrogen, an alkali metal or an earth alkali metal.

It is often necessary to bind heavy metal ions and earth-alkali ions as water-soluble chelates, for example, in various washing processes. In photography chemicals, chelates of metal ions are used in the developing process. When oxygen or peroxide compounds are used in the total chlorine free (TCF) bleaching of pulp it is important to remove the heavy metals from the fiber before bleaching, since heavy metal salts catalyze the decomposition of peroxy compounds, thus forming radical compounds. In consequence of these reactions the strength properties of the fiber are deteriorated.

At present, the complexing agents most commonly used in the applications mentioned above are ethylenediamine-tetraacetic acid (EDTA) and its salts and diethylenetriamine-pentaacetic acid (DTPA) and its salts. These are excellent complexing agents, but their biodegradability is poor.

Patent applications FI-960758, FI-960757, FI-960756 and FI-960755 disclose the use of aspartic acid derivatives as chelating agents in bleaching of pulp. Such chelating agents include ethylenediaminedisuccinic acid (EDDS) and its earth-alkali salts, as well as N,N'-iminodisuccinic acid (ISA) and its earth-alkali salts. EDDS and ISA are effective chelating agents of heavy metals. In addition, they are biodegradable.

From JP patent applications 7 261 355 and 6 282 044 there are known EDDS-type aspartic acid derivatives in which the hydrocarbon chain is longer than in EDDS. One such substance is N,N'-(oxydi-2,1-ethanediyl)-bis-L-aspartic acid.

Chelating agents should contain as small an amount as possible of nitrogen in order for the nitrogen load in waste waters to be as low as possible. Chelating agents of the type of EDDS, wherein some of the nitrogen atoms have been replaced with oxygen atoms, are disclosed in JP patent applications 7 120 899 and 7 120 894. The applications disclose the use of various isomers of N-[2-(1,2-dicarboxyethoxy)-ethyl]-aspartic acid (EDODS) in photography chemicals. According to the publications, EDODS is biodegradable. A method of preparing EDODS by $La^{3+}$-catalyzed O-alkylation of maleic acid salts has been described in the literature (J. van Vestrenen et al., Recl. Trav. Chem. Pays-Bas, vol. 109, 1990, p. 474–478). However, in application tests performed by the applicant, EDODS did not prove to be a sufficiently effective chelating agent. One possible explanation for the poor chelating result is the length of the carbon chain between the dicarboxyethyl groups. If the said carbon chain is not sufficiently long, strains are produced in the molecule during complexing, and the metal complex will not be sufficiently stable.

The object was to develop an effective chelating agent which would be biodegradable and contain little nitrogen.

The formula of the new compounds according to the invention is

Formula I

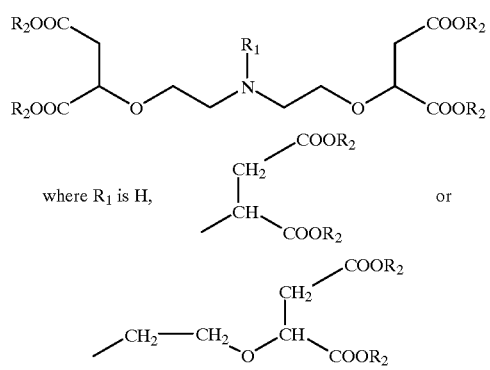

and $R_2$ is hydrogen, an alkali metal or an earth-alkali metal.

In the said molecule structure, a secondary or tertiary nitrogen atom is as the central atom. Additionally the molecular structures contain four or six carboxylic acid groups, which coordinate effectively with heavy metals. The carbon chains are sufficiently long in terms of the formation of advantageous bond angles.

Novel compounds according to the invention include N-bis-[(1,2-dicarboxy-ethoxy)-ethyl]-amine (BCEEA), N-tris-[(1,2-dicarboxy-ethoxy)-ethyl]-amine (TCEEA) and N-bis-[(1,2-dicarboxy-ethoxy)-ethyl]-aspartic acid (BCEEAA), as well as the alkali metal and earth-alkali metal salts of the said compounds, preferably $Na^+$, $K^+$, $Ca^{2+}$ and $Mg^{2+}$ salts.

TCEEA

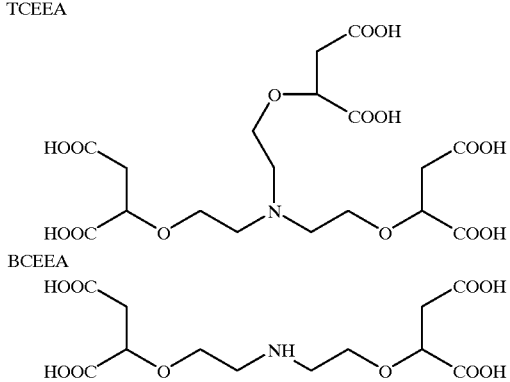

BCEEA

-continued

BCEEAA

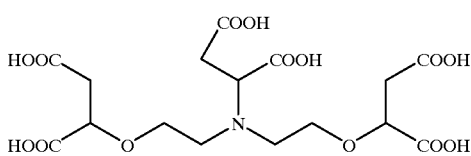

The novel amine compounds according to the invention can be prepared by using as the starting material alkali metal or earth-alkali metal salts of maleic acid and diethanolamine or triethanolamine in the presence of a lanthanide or earth-alkali metal catalyst, in accordance with Synthesis Formula 1.

Synthesis Formula 1

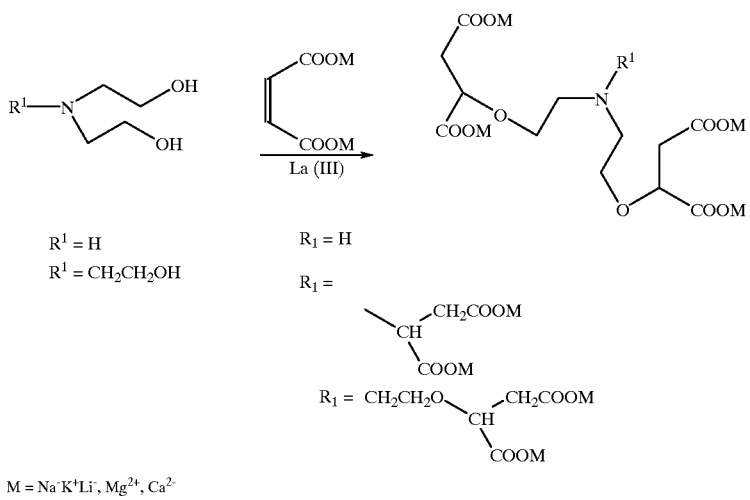

$M = Na^-K^+Li^-, Mg^{2+}, Ca^{2-}$

The maleic acid salt which is the intermediate stage in the synthesis can be prepared in an aqueous solution by preferably using, as the starting substances, available starting substances such as maleic acid anhydride and alkali metal or earth-alkali metal compounds. Alkali metal compounds suitable for the reaction include lithium hydroxide, sodium hydroxide, potassium hydroxide, sodium carbonate, potassium carbonate, and lithium carbonate. Earth-alkali metal compounds suitable for the reaction include magnesium hydroxide, magnesium oxide, magnesium carbonate, calcium oxide, calcium hydroxide, and calcium carbonate.

The forming of maleate is an exothermal reaction. When the maleic anhydride is first added to water, maleic acid is formed. When an alkali is added to this solution at a suitable rate, the temperature of the reaction mixture will increase to 80–90' C., which is a temperature preferable for the performing of the alkylation reaction.

The amino alcohol, most preferably diethanolamine or triethanolamine, and the lanthanum compound used as the catalyst can thereafter be added rapidly to the alkaline reaction mixture.

Lanthanide compounds or their mixtures can be used as the catalyst. Likewise, suitable catalysts for 0-alkylation include earth-alkali metal compounds such as calcium hydroxide and magnesium hydroxide. Furthermore, nickel compounds can be used as the catalyst.

It is preferable to use as the catalyst lanthanum(III) compounds, such as lanthanum(III) nitrate, lanthanum(III) chloride, lanthanum oxide, lanthanum sulfate, and lanthanum octanoate. Likewise, lanthanum compounds which contain optically active ligands can be used as a catalyst in the reaction.

$La^{3+}$-catalyzed O-alkylation of maleic acid salt with amino alcohols is a useful reaction, since the synthesis is a single-step synthesis and the catalyst can be recycled. The catalyst can be separated from the reaction mixture after the reaction by rendering the reaction mixture acidic by means of mineral acids and by adding oxalic acid to the hot reaction mixture. The pH of the reaction mixture can be adjusted by using hydrochloric acid, sulfuric acid, nitlic acid or phosphoric acid, most preferably hydrochloric acid or sulfuric acid. The lanthanum oxalate precipitate formed can be separated from the reaction mixture by filtration. The lanthanum(III) salt used as a catalyst can be separated from the oxalate precipitate by treating the precipitate with nitric acid or hydrochloric acid. After the treatment the catalyst can be reused.

Compounds according to the invention can also be prepared by other methods.

The compounds according to the invention are especially well suited for use in alkaline aqueous solutions, such as detergents and cleansing agents. Furthermore, the compounds according to the invention are suited for use in photography chemicals.

The novel compounds are useful chelating agents in, for example, alkaline aqueous solutions which contain hydrogen peroxide or peroxy compounds. The novel compounds are particularly useful as chelating agents of heavy metals in a pretreatment before the bleaching of cellulose with ozone, hydrogen peroxide or peroxy acids such as performic, peracetic, perpropionic or Caro's acid and combinations of the same.

Since the novel compounds do not contain phosphorus and contain very little nitrogen, they load the environment considerably less than do the chelating agents currently used.

The invention is described below with the aid of examples, which do not, however, limit the invention.

EXAMPLE 1

A disodium maleate solution was prepared by dissolving 29.4 g (0.3 mol) of maleic anhydride in 50 mil of water and by adding 50 g of a 48% caustic solution (0.6 mol NaOH) to the reaction mixture. During the addition the temperature of the reaction mixture was maintained at 70–90° C. 17 g (0.05 mol) of lanthanum(III) nitrate, $La(NO_3)_3 \times 6\ H_2O$, was added to the reaction mixture together with diethanolamine (10.5 g, 0.1 mol). The reaction mixture was stirred at 85° C. under a reflux con--denser for 48 hours. The reaction mixture was cooled and rendered acidic (pH 1.8) by means of a concentrated sulfuric acid. Thereafter the reaction mixture was reheated to 60° C., and 10 g of oxalic acid and 50 ml of water were added, the mixture was stirred at 60° C. for 20 minutes, and the formed La(III) oxalate precipitate was removed from the hot solution by filtration. The filtrate was cooled and any precipitate subsequently formed was removed by filtration. From the remaining solution (40 ml), which contained water 54%, the organic compounds were analyzed as silyl or methyl ester derivatives by means of $^{13}C$ NMR spectra and a mass spectrometer.

BCEEAA and BCEEA were identified from the $^{13}C$ NMR spectra. Unreacted initial substances were identified on the basis of reference spectra: diethanolamine and maleic acid, as well as oxalic acid used for the precipitation of the catalyst. Malic acid and fumaric acid were formed as byproducts of the reaction; these were also identified on the basis of reference spectra.

On the basis of a quantitative $^{13}C$ NMR analysis, the composition of the obtained reaction mixture containing BCEEAA and BCEEA, the mixture being hereinafter called RS12, was as follows:

|  | % by weight |
| --- | --- |
| BCEEAA | 18.5 |
| BCEEA | 7.9 |
| diethanolamine | 1.2 |
| maleic acid | 2.2 |
| malic acid | 2.5 |
| oxalic acid | 0.3 |
| fumaric acid | 2.1 |
| water | 54.3 |
| $Na_2SO_4$ | 11.0 |

Since BCEEA and BCEEAA are quite poorly soluble in organic solvents, the $^1H$-NMR technique cannot be used for the analysis of the reaction mixture. $^{13}C$ NMR spectroscopy is therefore the useful method for the analysis of the reaction mixture. The $^{13}C$ NMR spectrum data for BCEEAA and BCEEA are shown in Table 1.

Since the chemical shifts of the carbon atoms adjacent to nitrogen in BCEEAA and BCEEA are different, their molar proportions can be determined from the $^{13}C$ NMR spectrum of the reaction mixture. A comparison of the integrals of the BCEEA signal (48 ppm) and the BCEEAA signal (53 ppm) showed that the molar ratio BCEEAA:BCEEA was 2:1.

TABLE I

| Signal ppm | explanation |
| --- | --- |
| 175 | a |
| 176 | b |
| 37.9 | c |
| 75.8 | d |
| 65.5 | e |
| 54.4 | f |
| 62.0 | g |
| 32.6 | h |
| 170.3 | i |
| 173.9 | j |

| signal ppm | explanation |
| --- | --- |
| 175 | a |
| 176 | b |
| 37.9 | c |
| 75.8 | d |
| 66.4 | e |
| 47.8 | f |

For chromatography, the carboxylic acids contained in the reaction mixture were silylated by treating the reaction mixture with a silylation reagent (BSTFA) commonly used in gas chromatography. The sample was analyzed by using a gas chromatography - mass spectrometry apparatus.

Column: J&W DB5 30 m, 1.0 μm film, 0.32 mm i.d.

Temperature program: 80° C.→320° C., 10° C./min

Injector temperature: 250° C.

On the basis of the mass spectra, the molecular strictures of BCEEA and BCEEAA could be ascertained on the basis of their fragmentation. The structures of the silyl derivatives of the above-mentioned compounds and the mass spectra observed are shown in Table 2.

TABLE 2

| | |
|---|---|
| Silyl derivative of BCFEA<br>mol. weight: 697<br>m/z (relative intensity %): 406 (20), 333(15), 245(25), 147(45), 73(100) | (Structure of silyl derivative of BCFEA, showing (CH₃)₃SiOOC groups connected via CH₂-CH-O-CH₂ to N(CH₂)₂-Si(CH₃)₃ center with fragment marker at 406, and further CH₂-CH-O-CH₂ to COOSi(CH₃)₃ groups) |
| Silyl derivative of BCEEAA<br>mol. weight: 885<br>m/z (relative intensity %): 678(3), 594(20), 309(10), 245(35), 147(45), 73(100) | (Structure of silyl derivative of BCEEAA, with (CH₃)₃SiOOC-CH₂-HC(-O-CH₂-)- branch to N center with fragment marker at 594, and H₂C(COOSi(CH₃)₃)-CH(COOSi(CH₃)₃) and H₂C-CH(COOSi(CH₃)₃)-O-CH₂ branches) |

Furthermore, the trimethylsilyl derivatives of the starting substances and byproducts of the above-mentioned reaction were identified from the mass spectra.

The carboxylic acid groups in the reaction mixture were esterified into methyl esters by using methanol in a reaction catalyzed with boron trifluoride. The methyl esters of the reaction byproducts and the methyl ester derivative of BCEEAA were identified from a GC-MS spectrum (Table 3).

TABLE 3

| | |
|---|---|
| Hexamethyl ester of BCEEAA<br>mol. weight 393<br>m/z (relative intensity):<br>362 30, M-31), 302(10), 189(10), 113(100), 85(55), 59(60) | (Structure of hexamethyl ester of BCEEAA, with H₃COOC-CH₂-HC(-O-CH₂-) branch to N center, H₂C(COOCH₃)-CH(COOCH₃) branch, and H₂C-CH(COOCH₃)-O-CH₂ branch with fragment marker at 189) |

The structures of the compounds BCEEA and BCEEAA obtained from the synthesis were ascertained by isolating them from the reaction mixture by ion exchange chromatography and by analyzing the purified reaction products obtained.

A sample (13.25 g) of the reaction mixture obtained in accordance with what has been presented above was pretreated by adding to it 1.16 g of calcium carbonate. Thereupon the sulfate ions present in the sample precipitated as calcium sulfate.

The ion exchange resin used was a strong anion exchange resin (Bio-Rad AG1-X8, 200–400 mesh) in its formiate form. The sample was eluted through an ion exchange column by using an eluent (1000 ml); the formic acid concentration of the eluent was increased gradually so that the formic acid concentration in the eluent ranged from 0–2 mol/l. During the run, one hundred samples of 10–20 ml were collected, and they were analyzed by liquid chromatography. BCEEA and BCEEAA were isolated from the fractions. The $^{13}$C NMR spectra and GC-MS spectra of the reaction products were ascertained by comparing the spectrum data of purified and isolated reaction products with the spectrum data of reaction products identified from the reaction mixture. The spectra of purified BCEEA and BCEEAA proved to be identical with the spectrum data stated in Tables 1–3.

EXAMPLE 2

TCEEA was prepared by the method described in Example 1 by using triethanolamine (1.0 mol) and maleic anhydride (3.4 mol) as the starting substances.

TCEEA was identified from the $^{13}$C NMR spectrum. The unreacted starting substances were identified on the basis of reference spectra: triethanolamine and maleic acid, as well as oxalic acid used for precipitating the catalyst. Malic acid and fumaric acid were formed as byproducts of the reaction; these were also identified on the basis of reference spectra.

On the basis of a quantitative $^{13}$C NMR analysis, the composition of the reaction product was as follows:

| | molar % |
|---|---|
| TCEEA | 46.3 |
| triethanolamine | 18.5 |
| maleic acid | 11.5 |
| fumaric acid | 3.2 |
| malic acid | 13.5 |
| oxalic acid | 6.6 |

The i$^{13}$C NMR spectrum data for TCEEA are shown in Table 4.

TABLE 4

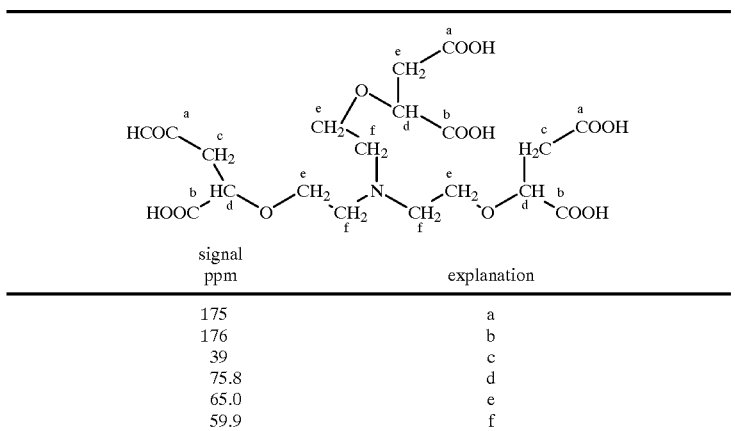

| signal ppm | explanation |
|---|---|
| 175 | a |
| 176 | b |
| 39 | c |
| 75.8 | d |
| 65.0 | e |
| 59.9 | f |

The carboxylic acid groups in the reaction mixture were esterified into methyl esters by using methanol in a reaction catalyzed with boron trifluoride. The methyl esters of the reaction byproducts and the methyl ester derivative of TCEEA were identified from a GC-MS spectrum (Table 5).

TABLE 5

Hexamethyl ester of TCEEA
mol. weight 581
mz (relative intensity): 550(10, M-31), 552(5, M-59), 406 (100, M-175), 189 (15), 172(10), 113(30), 59(40)

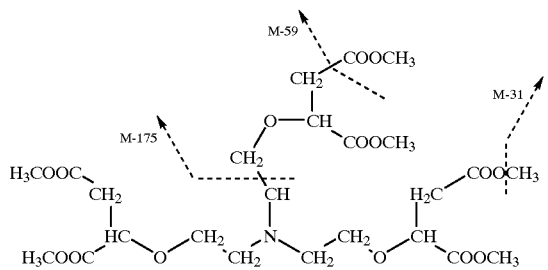

EXAMPLE 3

A reaction mixture, RS12, the composition of which is described in Example 1, was prepared in the laboratory. The alkaline reaction mixture RS12, having a pH of 9.0, was used in washing tests of a oxygen-delignified softwood pulp, the results being shown in Table 4.

In order to investigate the chelating of heavy metals and earth-alkali metals, the pulp was washed with the aqueous solution described above. The concentrations of metals in the washing solution were analyzed after the wash. The passing of iron (Fe), manganese (Nin), calcium (Ca) and magnesium (Mg) into the washing waters was thus determined. The passing of iron and manganese into the washing solutions is advantageous in terms of bleaching. In contrast, the passing of calcium and magnesium into the washing solutions is disadvantageous in terms of bleaching. In the reference tests, the pulp was washed with a DTPA solution. The concentrations of the chelating agents and the pH during the wash are indicated in Table 6. At a pH of 5.2, RS12 removed manganese from the pulp as effectively (100%) as DTPA, iron almost as effectively (83%) as DTPA, magnesium almost as effectively (83%) as DTPA, and calcium more effectively than did DTPA.

TABLE 6

Oxygen-delignified softwood sulfate pulp
Viscosity 710 dm$^3$/kg
Brightness 79.7% ISO
Kappa 6.7

| Time, min. | T, °C. | Consistency % | Initial pH | Final pH | Chelating agent, kg/tp | Filtrate analyses | | | | Normal DTPA = 100% | | | |
|---|---|---|---|---|---|---|---|---|---|---|---|---|---|
| | | | | | | Fe, mg/l | Mn, mg/l | Mg, mg/l | Ca, mg/l | Fe % | Mn % | Mg % | Ca % |
| 60 | 70 | 12 | Not adjusted | 1.3 | 1% HNO$_3$ | 1.8 | 0.4 | 80 | 25 | 100 | 133 | 276 | 403 |

TABLE 6-continued

Oxygen-delignified softwood sulfate pulp
Viscosity 710 dm³/kg
Brightness 79.7% ISO
Kappa 6.7

| Time, min. | T, °C. | Consistency % | Initial pH | Final pH | Chelating agent, kg/tp | Fe, mg/l | Mn, mg/l | Mg, mg/l | Ca, mg/l | Fe % | Mn % | Mg % | Ca % |
|---|---|---|---|---|---|---|---|---|---|---|---|---|---|
| 60 | 70 | 12 | 5 | 5.4 | DTPA 2 kg | 1.8 | 0.3 | 29 | 6.2 | 100 | 100 | 100 | 100 |
| 60 | 70 | 12 | 6.5 | 7.2 | DTPA 2 kg | 1.7 | 0.3 | 22 | 6.2 | 94 | 100 | 76 | 100 |
| 60 | 70 | 12 | 5–6 | 5.9 | Water wash | 0.61 | 0 | 17 | 3.2 | 34 | 0 | 59 | 52 |
| 60 | 70 | 12 | 5 | 5.2 | RS12 1.5 kg | 1.5 | 0.3 | 25 | 7.2 | 83 | 100 | 86 | 116 |
| 60 | 70 | 12 | 6.5 | 7.1 | RS12 1.5 kg | 0.8 | 0.3 | 15 | 6.5 | 44 | 100 | 52 | 105 |

Filtrate analyses columns: Fe, mg/l; Mn, mg/l; Mg, mg/l; Ca, mg/l. Normal DTPA = 100%.

EXAMPLE 4

The decomposition of hydrogen peroxide constitutes a problem in alkaline aqueous solutions which contain hydrogen peroxide. Therefore the stabilizing effect of a BCEEAA- and BCEEA-containing RS12 solution, described in Example 1, on alkaline hydrogen peroxide was tested in the presence of heavy metals (Fe, Mn) (Table 7).

TABLE 7

Tests on the stabilization of alkaline peroxide
Conditions: pH 10, 50° C., $H_2O_2$ initially 5.3 g/l

| Test no. | RS12 ppm | DTPA ppm | EDDS ppm | Fe ppm | Mn ppm | Half-life of $H_2O_2$, min |
|---|---|---|---|---|---|---|
| 1 | 0 | 0 | 0 | 0 | 0 | 530 |
| 2 | 0 | 273 | 0 | 2 | 4 | 236 |
| 3 | 0 | 0 | 140 | 2 | 2 | 4 |
| 4 | 0 | 0 | 280 | 4 | 4 | 2 |
| 5 | 140 | 0 | 0 | 4 | 2 | 338 |
| 6 | 140 | 0 | 140 | 0 | 4 | 363 |
| 7 | 140 | 0 | 280 | 2 | 0 | 226 |
| 8 | 280 | 0 | 0 | 2 | 4 | 452 |
| 9 | 280 | 0 | 140 | 4 | 0 | 197 |
| 10 | 280 | 0 | 280 | 0 | 2 | 1462 |

The reference agent used was DTPA, which is a commonly used chelating agent of iron and manganese, for example in connection with pulp production. EDDS, a chelating agent which has been found to be good in the applicant's previous experiments, was used as an additional reference agent.

It can be seen in the test results that RS12 stabilizes alkaline hydrogen peroxide clearly better than does DTPA or EDDS. Solutions which contain BCEEAA and BCEEA can thus be used as stabilizing agents, for example, in alkaline detergent solutions which contain hydrogen peroxide.

EXAMPLE 5

A corresponding test was performed on peroxyacetic acid (PAA) solutions (Table 8). It was observed that RS12 stabilized PAA solutions at least as well as did DTPA. The solution concerned is on this basis well suited for use as a stabilizing agent in acidic disinfectants which contain peroxy compounds.

TABLE 8

Example of the stabilization of a PAA solution
Reaction temperature: 50° C.

| Chelating agent | ppm | Mn ppm | Fe ppm | pH | Half-life of PAA, min |
|---|---|---|---|---|---|
| No chelating agent |  | 0 | 4.8 | 4.5 | 240 |
| DTPA | 140 | 0 | 4.8 | 4.5 | 1339 |
| No chelating agent |  | 0.4 | 0 | 4.5 | 390 |
| DTPA | 140 | 0.4 | 0 | 4.5 | 4 |
| EDTA | 140 | 0.4 | 0 | 4.5 | 7.5 |
| RS12 | 140 | 0.4 | 0 | 4.5 | 1005 |
| RS12 | 140 | 0 | 4.8 | 4.5 | 647 |
| No chelating agent |  | 0 | 4.8 | 7 | 87 |
| No chelating agent |  | 0.4 | 0 | 7 | 74 |
| DTPA | 140 | 0 | 4.8 | 7 | 201 |
| DTPA | 140 | 0.4 | 0 | 7 | 25 |
| RS12 | 140 | 0 | 4.8 | 7 | 146 |
| RS12 | 140 | 0.4 | 0 | 7 | 229 |

EXAMPLE 6

In the bleaching of pulp with an alkaline hydrogen peroxide solution, the stability of the peroxide solution alone will not guarantee the success in the bleaching. Therefore an RS12 solution which contained BCEEAA and BCEEA was used in the bleaching of a softwood sulfate pulp. In the bleaching tests (Table 9), RS12 was compared with DTPA. The results show that, when RS12 is used as the chelating agent, the viscosity of the pulp after the final bleaching is better than when DTPA is used. The kappa number and the brightness were at the same levels. It is to be noted that the residual peroxide in the solution in this test was double when RS12 was used (as compared with DTPA). This shows that RS12 is suitable for use for chelating preceding an alkaline peroxide step.

TABLE 9

An example of bleaching
Order of treatments: oxygen delignification, peroxyacetic acid
delignification, chelating, peroxide bleaching.
Softwood sulfate pulp
Oxygen-delignified: Kappa 9.7, viscosity 775 $dm^3/kg$
PAA-delignification: Kappa 5.3, viscosity 709 $dm^3/kg$

Chelating step

| t, min | 60 | 60 | 60 | 60 |
|---|---|---|---|---|
| T, °C. | 75 | 75 | 75 | 75 |
| pH, initial | 5 | 6.5 | 5 | 6.4 |
| pH, final | 5.1 | 6.5 | 5 | 6.2 |
| Chelating agent | DTPA | DTPA | RS12 | RS12 |
| Dose, kg/tp | 2 | 2 | 1.5 | 1.5 |

Final bleaching (alkaline hydrogen peroxide)

| | | | | | No chelating |
|---|---|---|---|---|---|
| t, min | 180 | 180 | 180 | 180 | 180 |
| T, °C. | 90 | 90 | 90 | 90 | 90 |
| pH, initial | 10.4 | 10.4 | 10.4 | 10.4 | 10.4 |
| pH, final | 9.7 | 9.8 | 9.8 | 9.8 | 9.5 |
| $H_2O_2$ dose, kg/tp | 20 | 20 | 20 | 20 | 20 |
| Residual $H_2O_2$, kg/t | 4.1 | 4.1 | 8.9 | 10 | 3 |
| Residual $H_2O_2$, % | 20.5 | 20.5 | 44.5 | 50 | 15 |
| Kappa | 2.2 | 2.3 | 2.4 | 2.3 | 2.2 |
| Viscosity, $dm^3/kg$ | 553 | 556 | 633 | 644 | 530 |
| Brightness, % ISO | 85 | 85 | 84.7 | 85.2 | 84.6 |

EXAMPLE 7

A magnesium maleate solution was prepared by dissolving 29.4 g (0.3 mol) of maleic anhydride in 50 ml of water and by adding to the reaction mixture 35.0 g of magnesium hydroxide (0.3 mol $Mg(OH)_2$) slurried in 70 ml of water. During the adding, the temperature of the reaction mixture was maintained at 70–90° C. 17 g (0.05 mol) of lanthanum (III) nitrate, $La(NO_3)_3 \times 6\ H_2O$ was added to the reaction mixture together with diethanolamine (10.5 g, 0.1 mol). The pH of the reaction mixture was adjusted to a pH value of II by adding a 48% sodium hydroxide solution. The reaction mixture was stirred at 85° C. under a reflux condenser for 10 hours. The reaction mixture was cooled and was rendered acidic (pH 1.8) by using concentrated sulfuric acid. Thereafter the reaction mixture was reheated to 60° C., 10 g of oxalic acid and 50 ml of water were added, the mixture was stirred at 60° C. for 20 minutes, and the formed precipitate was removed from the hot solution by filtration. The filtrate was cooled and any precipitate which subsequently formed was removed by filtration. From the remaining solution (42 ml), which contained water 54%, the organic compounds were analyzed as silyl or methyl ester derivatives by using $^{13}C$ NMR spectra and a mass spectrometer.

BCEEAA and BCEEA were identified from the 13C NMR spectrum. The unreacted starting substances were identified on the basis of reference spectra: diethanolamine and maleic acid. Malic acid and fumaric acid were formed as byproducts of the reaction; these were also identified on the basis of reference spectra.

On the basis of a quantitative 13C NMR analysis, the organic compound composition of the reaction product was as follows:

| | % by weight |
|---|---|
| BCEEAA | 13.8 |
| BCEEA | 4.5 |
| diethanolamine | 7.5 |
| maleic acid | 2.3 |
| malic acid | 1.3 |
| fumaric acid | 0.3 |

What is claimed is:

1. N-bis- or N-tris-(1,2-dicarboxy-ethoxy)-ethyl)-amine derivatives having the formula (I)

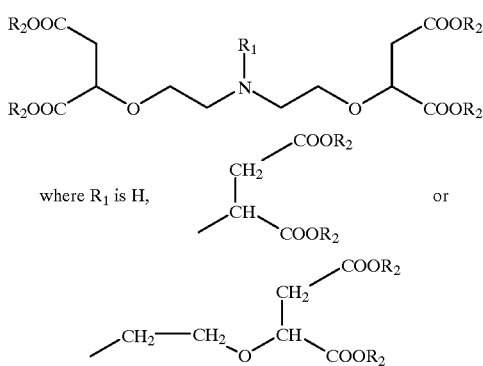

where $R_1$ is H, and $R_2$ is hydrogen, an alkali metal or an earth-alkali metal.

2. A compound according to claim 1, characterized in that, in accordance with Formula (I), the compound is N-bis-[(1, 2-dicarboxy-ethoxy)-ethyl]-amine or a $Na^+$, $K^+$, $Ca^{2+}$ or $Mg^{2+}$ salt thereof.

3. A compound according to claim 1, characterized in that the compound is N-bis-[(1,2-dicarboxy-ethoxy)-ethyl]-aspartic acid or a $Na^+$, $K^+$, $Ca^{2+}$ or $Mg^{2+}$ salt thereof.

4. A compound according to claim 1, characterized in that the compound is N-tris-[(1,2-dicarboxy-ethoxy)-ethyl]-amine or a $Na^+$, $K^+$, $Ca^{2+}$ or $Mg^{2+}$ salt thereof.

5. A method for the preparation of compounds according to claim 1, having the formula I, characterized in that the di- or triethanolamine is caused to react with an alkali metal or earth-alkali metal salt of maleic acid to form a compound of Formula I by using as a catalyst lanthanide compounds, mixtures of lanthanide compounds or earth-alkali metal compounds.

6. A method according to claim 5, characterized in that the di- or triethanolamine is caused to react with an alkali metal or earth-alkali metal salt of maleic acid in the presence of a $La^{3+}$ catalyst to form a compound of Formula I.

7. A method according to claim 5, characterized in that the alkali metal or earth-alkali metal salt of maleic acid is prepared by a reaction between maleic anhydride and a hydroxide or carbonate of an alkali metal or earth-alkali metal.

8. A method according to claim 5, characterized in that the reaction is performed at a temperature of 75–95° C.

9. A method of chelating heavy metals in an alkaline aqueous solution which comprises adding to said alkaline aqueous solution an amount effective to chelate said heavy metals of a N-bis- or N-tris-[1,2-dicarboxy-ethoxy)-ethyl]-amine derivative having the formula:

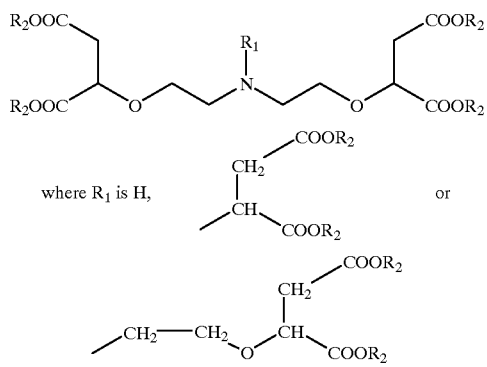

where $R_1$ is H,

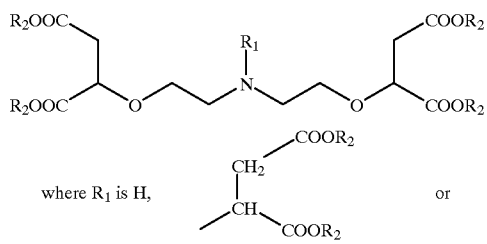

or and $R_2$ is hydrogen, an alkali metal or an earth-alkali metal.

10. A method of chelating heavy metals wherein a N-bis- or N-tris-[1,2-dicarboxy-ethoxy)-ethyl]-amine derivative having the formula:

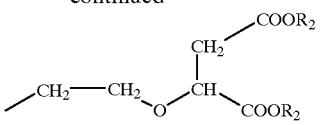

where $R_1$ is H, and $R_2$ is hydrogen, an alkali metal or an earth-alkali metal, is added to said heavy metals in a pretreatment step before said chelated heavy metals are added to a pulp bleaching solution in which cellulose is bleached with ozone, hydrogen peroxide, peroxy acids or combinations thereof.

11. A method of chelating heavy metals as claimed in claim 9, wherein said alkaline aqueous solution contains hydrogen peroxide or peroxy compounds.

12. The method of chelating heavy metals as claimed in claim 9, wherein said alkaline aqueous solution contains detergents, cleaning agents and/or disinfectants.

13. The method of chelating heavy metals as claimed in claim 9, wherein said alkaline aqueous solution contains photography chemicals.

* * * * *